United States Patent [19]

McGill et al.

[11] Patent Number: 5,647,903
[45] Date of Patent: Jul. 15, 1997

[54] MICROPOROUS HIGH STRUCTURE PRECIPITATED SILICAS AND METHODS

[76] Inventors: Patrick D. McGill, 610 Snow Goose Ct., Havre de Grace, Md. 21078; William Fultz, 1114 Telegraph Rd., Rising Sun, Md. 21911

[21] Appl. No.: 538,486

[22] Filed: Oct. 3, 1995

[51] Int. Cl.⁶ ............................ C09C 1/28; C01B 33/154
[52] U.S. Cl. .................. 106/492; 106/287.34; 106/482; 423/338; 424/49; 252/315.6
[58] Field of Search ........................... 106/482, 492, 106/287.34; 423/338; 424/49; 252/315.6

[56] References Cited

U.S. PATENT DOCUMENTS

| | | | |
|---|---|---|---|
| 3,428,425 | 2/1969 | Marotta | 106/492 |
| 3,967,563 | 7/1976 | Wason | |
| 4,144,321 | 3/1979 | Wason | 106/492 |
| 4,191,742 | 3/1980 | Wason et al. | 106/492 |
| 4,243,428 | 1/1981 | Donnet et al. | 106/492 |
| 4,251,281 | 2/1981 | Machurat et al. | |
| 5,234,673 | 8/1993 | McGill et al. | 423/338 |
| 5,342,598 | 8/1994 | Persello | 106/492 |

OTHER PUBLICATIONS

Journal of Society of Cosmetic Chemists, vol. 29, pp. 497–521 (Aug. 1978).
J. Am. Chem. Soc., vol. 60, pp. 309–319 (1938) no month avail.

*Primary Examiner*—David Brunsman

[57] ABSTRACT

Precipitated silicas having wet cake moisture values in excess of 85%, BET surface areas of 600–700 m²/g, oil absorption values of 50 to 60 cc/100 g, total intruded volume of about 1.2 to 0.8 cc/g, and a median pore radius of 50 Å to 20 Å are produced by a low temperature silica precipitation process. The silicas have unique flatting characteristics and are additionally useful as conditioning agents for food and salt and in dentifrice compositions.

17 Claims, No Drawings

MICROPOROUS HIGH STRUCTURE PRECIPITATED SILICAS AND METHODS

TECHNICAL FIELD

The present invention relates to novel silica products and, more particularly, to a method for producing gel or gel-like synthetic precipitated silicas having new and unique properties and uses of the novel precipitated silicas.

BACKGROUND ART

As known in the art, commercially available silicas can broadly be divided into two basic categories. These categories are those produced from a liquid phase and those from a vapor phase process.

Vapor process silicas, called fumed and pyrogenic silicas, are prepared by reacting silicon tetrachloride vapor with an oxygen-hydrogen gas at high temperatures to produce silicon hydrogen chloride. Pyrogenic silicas have high external surface areas and differ from other silicas (e.g., gels, precipitated silicas, etc.) prepared by the liquid phase process.

Liquid phase silicas include precipitated silicas produced by acidulating an alkali metal silicate with an acid such as sulfuric acid. Liquid phase silicas also include silica gels and colloidal silicas.

In recent years, and to further expand the utility of precipitated silicas, prior art workers have developed new techniques for producing precipitated silicas having new and unique properties.

U.S. Pat. No. 3,967,563 discloses a process for precipitating a very high structure silica. In the disclosed process, the rate of acidulation is very carefully controlled, particularly at the outset of the reaction and at the point at which precipitation initially occurs. The silica product produced by this method has a very high structure, a wet cake moisture between 86–89%, an oil absorption of about 220–250 cc/100 g and a surface area of about 250–280 $m^2/g$.

U.S. Pat. No. 4,251,281 discloses a process for producing synthetic amorphous silica which has a surface area of between 80–310 $m^2/g$ and an oil absorption index of between 240–320 cc/100 g. The process involves reacting a strong acid with an alkali metal silicate solution wherein the acid is added to the solution at a variable rate to maintain a residual alkalinity of the medium substantially constant with time.

U.S. Pat. No. 5,234,673, a prior patent of the present inventors, discloses a process for producing a precipitated silica which has a high structure, and an oil absorption of less than 300 cc/100 g, the silica being produced by acidulation of alkali metal silicate.

The present invention provides a novel silica product which is a high structure product with smaller pores than known previously, which silica is useful in paints, as a conditioning agent in foods, and in dentifrices, and is produced by acidulation of an alkali metal silicate under novel reaction conditions.

DISCLOSURE OF THE INVENTION

Accordingly, one object of the present invention is to provide a process for producing a gel or gel-like silica product having a low oil absorption, a high wet cake moisture, and a unique microporosity. In one aspect, the process of the present invention uses lower concentrations, lower temperatures and different molar ratios than the prior art in the synthesis of the silica.

A further object of the present invention is to provide a novel silica gel product having a lowered oil absorption value, a high wet cake moisture content, and increased microporosity, the silica being useful as a flatting pigment in paints, varnishes, lacquers and similar coating compositions, as a conditioning agent in foods, and as an abrasive in dentifrice compositions.

Other objects and advantages of the present invention will become apparent as the description thereof proceeds.

In satisfaction of the foregoing objects and advantages, there is provided by the present invention a composition of matter comprising a finely-divided silica gel or gel-like amorphous silica, said silica being characterized by an oil absorption value of about 50 to 60 cc/100 g, a wet cake moisture value in excess of 85%, a surface area in the range of about 600 to 700 $m^2/g$ and a unique microporosity where the median pore radius equals about 50 to 20 Angstroms (Å).

Also provided are flatting pigments, conditioning agents, and dentifrice compositions which contain said precipitated silica gel.

The present invention also provides a method for producing the silica gel compositions of the present invention which comprises:

(a) providing an aqueous reaction medium containing an alkali metal silicate at a temperature of about 68° to 86° F. (20° to 30° C.);

(b) adding to said alkali metal silicate aqueous reaction medium an acidulating agent such as sulfuric acid at a temperature of about 86° to 98° F. (30° to 37° C.) to form a gel slurry;

(c) continuing to add acidulating agent to said alkali metal silicate to lower the pH of the gel slurry to about 5.5 to 5.8;

(d) digesting the mixture by heating at the reaction temperature for a residence time of about 40 to 80 minutes; and (e) collecting and washing the gel reaction product with water to provide the silica gel composition.

DESCRIPTION OF THE INVENTION

The present invention provides a new group of silicas in the form of a gel or gel-like amorphous material. These silicas are characterized as being high structural materials which have more microporosity than similar silicas known to the prior art. Total intruded volume is determined by mercury intrusion measurements well known to the art. See "A Review of Mercury Porosimetry" by Hillar M. Rootare, "Advanced Experimental Techniques in Powder Metallurgy", pages 225–252 (1970), Plenum Press. The microporosity pore size (median radius) is in the range of 50 Å to 20 Å and down to values which cannot be measured by mercury intrusion. The total intruded volume ranges from about 1.2 to 0.8 cc/g. The gel character of the product together with the microporosity and high structure thus provides a silica gel or gel-like product which has tremendous absorptive power and is useful in many areas. The silica product of the invention has the characteristics of a gel, but is produced by precipitation.

The silicas of the present invention are also characterized by oil absorption values of about 50 to 60 cc/100 g, a wet cake moisture value in excess of 85%, a BET surface area in the range of about 600–700 $m^2/g$, a pour density in the range of about 28–32 lbs/ft$^3$, a pack density of about 40–45 lbs/ft$^3$ and a particle size in the unmilled form in the range of about 60 micron median value. These characteristics make the silica of the present invention useful in paints, as conditioning agents in foods and similar materials, and as abrasive compositions in dentifrice compositions.

In producing the products of the present invention, a solution of alkali metal silicate is first charged to a reaction vessel (equipped with suitable heating and agitation equipment). The silicate solution is maintained or heated to a temperature in the range of from about 68° to 86° F. (20° to 30° C.), more preferably about 77° (25° C.). The silicate solution may, of course, be prepared in the reaction vessel or in situ.

As used herein, the term "alkali metal silicate" includes all the common forms of alkali silicates, as for example metal silicates, disilicates and the like. Water soluble potassium silicates and sodium silicates are particularly advantageous with the latter being preferred. The mole ratio of the alkali silicate, i.e., ratio of silicate to alkali metal has been found to contribute, depending on other reaction parameters, to the average pore size of the silica products. Acceptable products can be made with silicate mole ratios of between 2.5 to about 3.5. Preferred silicate mole ratios, especially for sodium silicate are about 3.3.

After the silicate solution has been heated to the above-noted temperature, an acidulating agent, preferably a mineral acid, is added in an amount sufficient to acidulate 100% of excess silicate, to bring the final slurry to a pH of between 5.5 and 5.8.

The acidulating agent is added at a controlled rate and at a temperature of about 86° to 98° F. (30° to 37° C.), preferably about 93° F. (34° C.). In a preferred embodiment in which a batch volume of 3,300 gallons is utilized, sulfuric acid at a concentration of about 11.4% by weight is added to 2,100 gallons of a silicate solution having a silica concentration of about 9.0% by weight at a rate of about 23.8 GPM until a pH of about 6.5 is reached. Thereafter the acid is manually added to reach a pH of between about 5.5 and 5.8. In this embodiment the acidulation time is about 46–48 minutes.

The reaction temperature ranges from about 77° to 86° F. (25° to 30° C.), preferably in the range of about 84° to 88° F. (29° to 31° C.) over a residence time of about 40 minutes to 60 minutes.

The acid is preferably a strong mineral acid such as sulfuric acid which is added as a dilute solution thereof with preferred results being obtained if the acidic solution comprises from about 10 to 15% by weight acid based on the total weight of the solution. In a preferred embodiment, the acidic solution comprises about 11.4% by weight acid, based on the total weight of the solution.

After the addition of the acidulating agent, the slurry is allowed to digest at a temperature of between about 77° to 86° F. (25° to 30° C.), or about the temperature of the reaction, for between about 10 and 20 minutes, with preferred reaction conditions including a temperature of about 85° (30° C.) and a digestion period of about 20 minutes.

After the digestion step the resulting slurry is filtered, washed with water to reduce the $Na_2SO_4$ level to less than 10% by weight, and preferably to less than 4% by weight and more preferably to 2–3% or less by weight. In a most preferred embodiment, the $Na_2SO_4$ level is ideally reduced to less than about 1% by weight. In this regard, it has been determined that high levels of $Na_2SO_4$ affect both the oil absorption values and the surface area values, with increasing levels of $Na_2SO_4$ significantly lowering the surface area values.

Washing of the reaction product is generally conducted after filtering. However, for large batches, diluting the reaction slurry with water before filtration will aid in reducing the $Na_2SO_4$ levels in subsequent washing procedures.

Drying of the reaction product, in addition to the reaction temperature, has been found to be a significant process variable in connection with producing the silica products of the present invention. The reaction product is dried to lower the non-structural moisture level to between about 4–30% by weight. Both oven drying and spray drying processes can be used in the present invention. However, oven drying processes have been found to produce silica products having lower oil absorption values than similar products produced by spray drying processes. Therefore, when scaling up the process according to the present invention to utilize larger reactors, spray dying techniques should be used. Also, smaller scale processes such as those using 30 gallon reactors or less can be used in conjunction with spray drying techniques to produce products having acceptable oil absorption values.

The final product may, if desired, be milled to obtain a desired particle distribution. The product of the invention has a median value particle size of about 60 microns. Milling of the silica is helpful for use as a flatting pigment in paints. This unique narrow particle size distribution eliminates, in many applications, the need for classifying the final product.

In this specification, the wet cake moisture of the silica is an important characteristic. At a fixed set of reaction conditions, the water associated with the precipitate or the filter cake is called the structural water. The amount of water associated with one part of the dry, recoverable product is defined as the water pore volume. The amount of water associated with 100 parts of the dry recoverable product is defined as Structure Index (SI). Thus, the water pore volume (PV) and SI are related to the % WCM by the following equation.

$$PV = \left( \frac{\% \ WCM}{100 - \% \ WCM} \right) \quad (1)$$

$$SI = \left( \frac{\% \ WCM}{100 - \% \ WCM} \right) \times 100 \quad (2)$$

A product with water pore volume above 6.5 or SI values above 650 is arbitrarily defined as a VHS (very high structure silica). A low structure silica (LS) is one which exhibits a water pore volume above 1.5 or SI values above 150. The log of the water pore volume or the log SI is linearly related to the % WCM.

A complete discussion of the wet cake moisture measurements and effects may be found in Journal of Society of Cosmetic Chemists, Vol. 29, p. 497–521 (August, 1978), and the disclosure therein is incorporated herein by reference.

In general, as the structure increases to more microporosity, the density also increases. Thus, the products of the present invention have a pour density in the range of about 30 lbs. per cubic foot and a pack density in the range of about 40–45 lbs. per cubic foot. The total intruded volume, measured by mercury intrusion, indicates product median pore ranges from 50 Å down to about 20 Å, and even to the point where it cannot be measured. Thus, the total intruded volume is approximately 1.2–0.8. The microporosity of the silica gels of the present invention is an important characteristic as it provides the product with substantial absorption characteristics which makes it useful in many areas.

In this specification, Oil Absorption is determined by ASTM, D 281-31, and BET surface area is determined as described in J. Am. Chem. Soc., Vol. 60, p. 309–319, (1938).

As more particularly discussed in the examples which follow, the silica gel products of the present invention have been found to have unique properties which provide for new compositions wherein the novel microporous very high structure, lowered oil absorption silicas can be advantageously substituted for other commercially available silica products. These compositions include novel coating compositions wherein the present silica product is utilized as a flatting agent in paints, food conditioning agents, dentifrice compositions, beer chill proofing applications and edible oil absorption applications. When surface treated with a wax component, settling can be avoided and the product can be used in various coating formulations.

The following examples are presented to illustrate the invention but the invention is not considered to be limited thereto. In the examples and throughout the specification, parts are by weight unless otherwise indicated.

EXAMPLE 1

In this example, a seven liter laboratory reactor system is used to prepare the silica. The batch procedure involves acidulation of 100% excess of 9.0% sodium silicate solution in the reactor with dilute (11.4%) sulfuric acid to final slurry pH of 5.5. A reaction temperature of 86° F. (30° C.) is maintained during the reaction. The dilute sulfuric acid is likewise heated with a hot plate to a temperature of 93° F. (34° C.). The heated sulfuric acid is pumped into the reactor by conventional pump means. After the addition of sulfuric acid is complete, the slurry is then digested at 86° F. (30° C.) for 20 minutes. The reaction mixture is stirred by use of a Lightnin mixer. A temperature and pH monitor are provided. The resulting slurry is then filtered, water washed (to 2.0% or less $Na_2SO_4$ content) and spray dried to a 4–6% moisture level. The dried product displayed the following characteristics:

| Product Evaluation | |
| --- | --- |
| OIL ABSORPTION | 60 cc/100 g |
| B.E.T. SURFACE AREA | 700 m$^2$/g |
| COULTER COUNTER APS | 60 μm |
| POUR DENSITY | 30 #/ft$^3$ |
| PACK DENSITY | 45 #/ft$^3$ |
| HG INTRUSION | 1.2–0.8 cc/g |

Although the invention has been described with reference to particular means, materials and embodiments, from the foregoing description, one skilled in the art can easily ascertain the essential characteristics of the present invention and various changes and modifications may be made to adapt the various usages and conditions without department from the spirit and scope of the present invention as described in the claims that follow.

We claim:

1. A composition of matter comprising a finely divided silica having an oil absorption value about 50 to 60 cc/100 g, a wet cake moisture value in excess of 85%, a BET surface area of about 600 to 700 m$^2$/g and a total intruded volume of about 1.2 to 0.8 cc/g, and a median pore radius of about 50 Å to 20 Å as measured by mercury intrusion.

2. A composition according to claim 1, which has an unmilled median value particle size of about 60 microns.

3. A composition according to claim 1, which has a pour density of about 30 lb/cu ft.$^3$ and a pack density of about 40 to 45 lb/cu ft$^3$.

4. A composition according to claim 1, which is a silica characterized by an oil absorption of about 60 cc/100 g, and a BET surface area of about 700 m$^2$/g.

5. A coating composition containing a flatting pigment which comprises a silica of claim 1.

6. A food composition conditioning agent comprising a silica of claim 1.

7. A dentifrice formulation which contains a silica of claim 1.

8. A method for producing a unique, high structure silica product having a total intruded volume of about 1.2 to 0.8 cc/g, and a pore median radius of about 50 Å to about 20 Å as measured by mercury intrusion, which comprises:

(a) providing an aqueous reaction medium containing an alkali metal silicate;

(b) adding an acidulating agent to said aqueous reaction medium maintained at a temperature of from about 86° F. to about 98° F. (30° to 37° C.);

(c) continuing to add said acidulating agent to said aqueous reaction medium to form a silica gel slurry having a pH between about 5.5 to about 5.8;

(d) digesting the reaction mixture by heating at the reaction temperature for a residence time of about 40 to 80 minutes; and (e) collecting and washing the gel reaction product with water to provide the silica gel product.

9. The method of claim 8, wherein the gel slurry is digested at the acidulation temperature.

10. The method of claim 8, wherein the alkali metal silicate is sodium silicate.

11. The method of claim 8, wherein the acidulating agent is sulfuric acid.

12. The method according to claim 11, wherein said acidulating agent comprises sulfuric acid having a concentration of about 11.4 wt. %.

13. The method of claim 8, wherein said acidulating agent is added in a sufficient amount to acidulate 100% of excess silicate.

14. The method of claim 8, wherein the silica product is water washed in step (e) to reduce the $Na_2SO_4$ content to less than about 2% by weight.

15. The method of claim 8, wherein the silica product is dried to have a moisture level of between about 4% to about 30% by weight.

16. The method of claim 15, wherein the drying is by spray drying.

17. The method of claim 8, wherein the alkali metal silicate is 3.3 molar sodium silicate solution, the acidulating agent is sulfuric acid having a concentration of about 11.4 wt. %, the reaction temperature is 86° F. (30° C.), the residence time is 50 minutes and the digestion time is at the reaction temperature for 10 to 20 minutes.

* * * * *